United States Patent [19]
Ayer et al.

[11] Patent Number: 5,019,396
[45] Date of Patent: May 28, 1991

[54] DELIVERY DISPENSER FOR TREATING CARDIAC ARRHYTHMIAS

[75] Inventors: Atul D. Ayer; Anthony L. Kuczynski; Patrick S. L. Wong, all of Palo Alto; Lawrence G. Hamel, Sunnyvale; Maureen L. Jordan, Mt. View, all of Calif.

[73] Assignee: ALZA Corporation, Palo Alto, Calif.

[21] Appl. No.: 350,996

[22] Filed: May 12, 1989

[51] Int. Cl.$^5$ .............................................. A61K 9/24
[52] U.S. Cl. .................................. 424/473; 424/468; 424/469; 424/470
[58] Field of Search ................ 424/464, 468, 438, 473

[56] References Cited

U.S. PATENT DOCUMENTS

| | | | |
|---|---|---|---|
| 2,799,241 | 6/1957 | Wurster | 118/24 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,036,228 | 7/1977 | Theeuwes | 128/260 |
| 4,063,064 | 12/1977 | Saunders et al. | 219/121 L |
| 4,077,407 | 3/1978 | Theeuwes et al. | 128/260 |
| 4,088,864 | 5/1978 | Theeuwes et al. | 219/121 LM |
| 4,111,201 | 9/1978 | Theeuwes | 128/260 |
| 4,200,098 | 4/1980 | Ayer et al. | 128/260 |
| 4,235,236 | 11/1980 | Theeuwes | 128/260 |
| 4,285,987 | 8/1981 | Ayer et al. | 427/3 |
| 4,449,983 | 5/1984 | Cortese et al. | 604/892 |
| 4,519,801 | 5/1985 | Edgren | 604/892 |
| 4,618,680 | 10/1986 | Mayol et al. | 514/821 |
| 4,704,118 | 11/1987 | Eckenhoff et al. | 424/438 |
| 4,824,675 | 4/1989 | Wong et al. | 424/438 |

OTHER PUBLICATIONS

Wurster, Dale E., *Am. Phar. Assoc.*, J. Sci. Ed., vol. 48, No. 8, pp. 451–459 (1959).
Wurster, Dale E., *Am. Phar. Assn.*, J. Sci. Ed., vol. 49, No. 2, pp. 82–82 (1960).
Roden et al., Dan M., *Am. J. Cardiol.*, vol. 58, pp. 4C–9C (1986).
Roden et al., Dan M., *Clin. Pharmacokinetics*, vol. 14, pp. 141–147 (1988).

*Primary Examiner*—Merrell C. Cashion, Jr.
*Assistant Examiner*—Leon R. Horne
*Attorney, Agent, or Firm*—Paul L. Sabatine; Edward L. Mandell; Steven F. Stone

[57] ABSTRACT

A dosage form is disclosed comprising a first composition comprising two different polyethylene oxide osmopolymers for delivering a drug at a controlled rate over time.

7 Claims, 2 Drawing Sheets

FIG_4
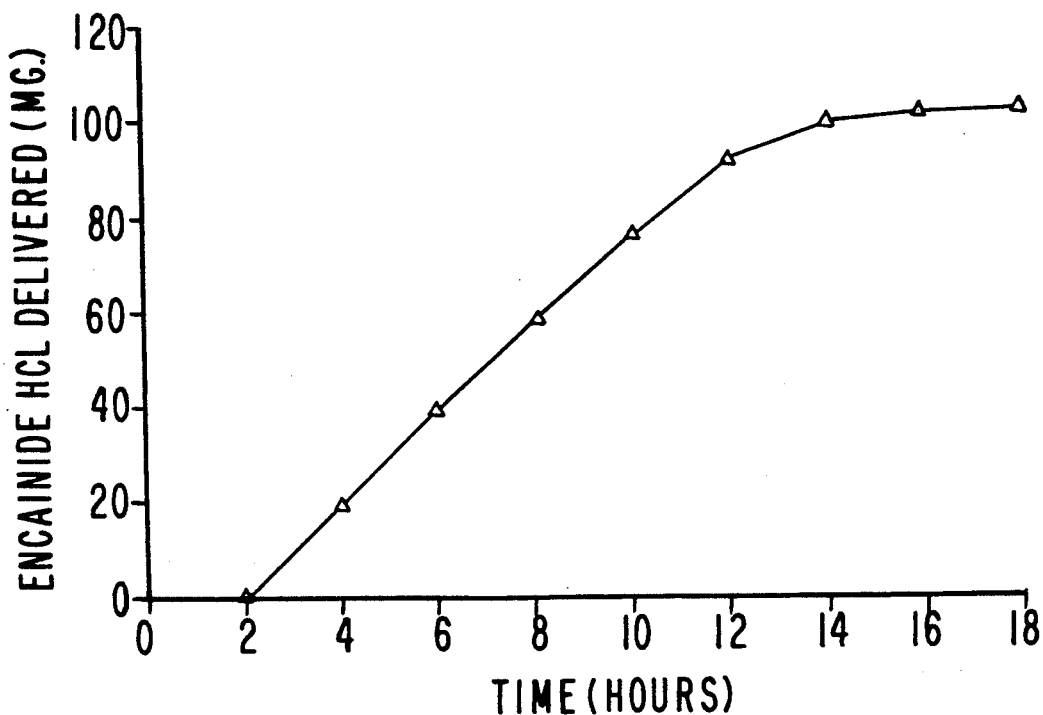
FIG.5
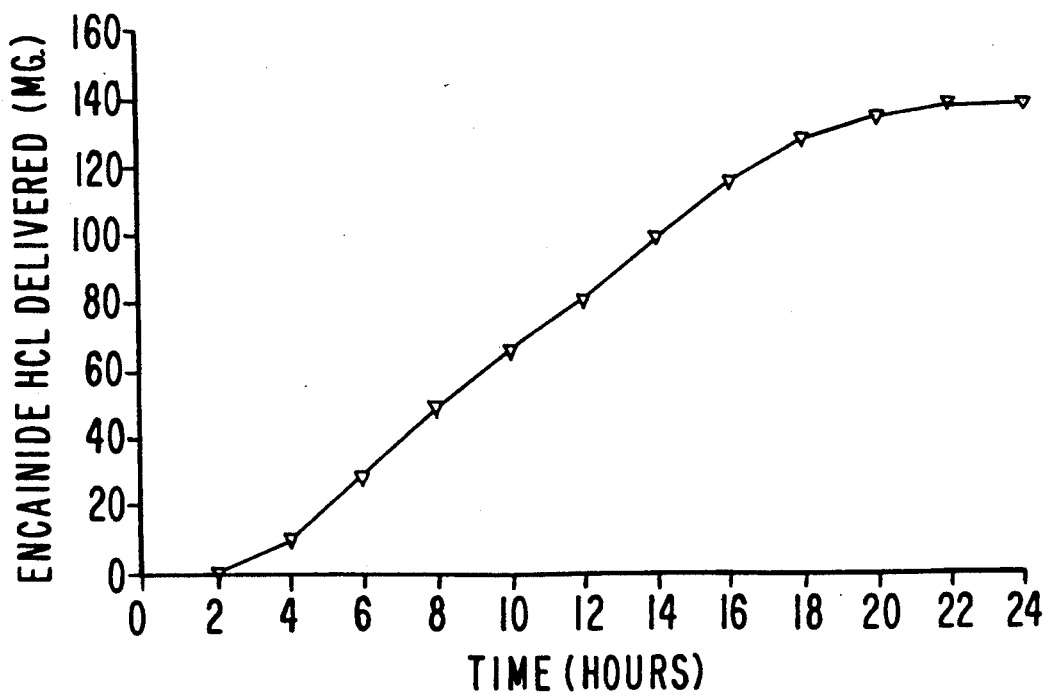

DELIVERY DISPENSER FOR TREATING CARDIAC ARRHYTHMIAS

FIELD OF THE INVENTION

This invention pertains to a delivery dispenser comprising encainide for treating cardiac arrhythmias. An embodiment of the invention concerns a method for the management of arrythmias comprising administering the anti-arrhythmic drug encainide.

BACKGROUND OF THE INVENTION

A primary purpose of the cardiovascular system is to sustain a normal flow of blood necessary to furnish oxygen and nutrients to the body's cells. The heart functions as the pump of the cardiovascular system, and it can change the strength of its contraction and the rate at which the heart contracts to regulate the flow of blood. If there is an abnormality in the heart's rate and in its rhythm, as in cardiac arrhythmias as evidenced by a loss of rhythm, or an irregularity of the heart beat, the biological consequence is a disruption of the cardiac output. This condition can lead to decreased tissue and organ perfusion. The atrial and ventricular arrhythmias can produce symptoms, induce heart failure, and lead to lethal arrhythmias such as asystole and ventricular fibrillation.

Recently, as reported in *Clinical Pharmacokinetics*. Vol. 14, pp 141-147, (1988), the drug encainide, chemically identified as ($\pm$)-2'-[2-(1-methyl-2-piperidyl)ethyl]-p-anisanilide, and its therapeutically acceptable salts, became available to the medical profession for the prevention and the treatment of cardiac arrhythmias. The drug encainide is indicated for the treatment of ventricular premature complexes and for other ventricular arrhythmias. In most patients on encainide therapy, encainide undergoes hepatic biotransformation to its active metabolites 0-desmethyl encainide and 3-methoxy-0-desmethyl encainide as reported in *Am. J. Cardiol.* Vol. 58, 4C, (1986). The drug encainide in possessing electrophysiological effects shows intracardiac conduction and it is a potent sodium-channel blockers. In the reported study the drug encainide was administered as a tablet in an uncontrolled dose that was subjected to the changing adverse environment of the gastrointestinal tract.

In light of the above presentation, it will be appreciated by those versed in the dispensing art to which this invention pertains that a pressing need exists for a delivery dispenser which is a rate controlled dosage form that can deliver the valuable drug encainide to a patient in need of cardiac therapy. The need exists also for an oral dosage form that can deliver encainide at a controlled rate in a substantially constant dose per unit time over a prolonged period of time for encainide's beneficial pharmacological and physiological effects substantially independent of the changing environment of the gastrointestinal tract. Those versed in the dispensing art well appreciate that such a novel and unique delivery dispenser that can administer encainide in a rate controlled dose over time, and simultaneously provide cardiac therapy, would represent an advancement and valuable contribution to the dispensing art.

OBJECTS OF THE INVENTION

Accordingly, in view of the above presentation, it is an immediate object of this invention to provide a delivery dispenser for administering encainide in a rate controlled dose, and which delivery dispenser substantially overcomes the deficiencies associated with the prior art.

Another object of the invention is to provide a delivery dispenser manufactured as a dosage form for administering encainide in a rate controlled dose over a prolonged period of time for cardiac arrhythmias.

Another object of the invention is to provide a dosage form adapted and sized for oral administration of encainide for the management of patients with ventricular tachycardia, nonsustained ventricular tachycardia, premature ventricular complexes and other ventricular arrhythmias.

Another object of the invention is to provide a novel dosage form that embodies osmotic functionalities and can administer encainide to a biological receptor site to produce the desired pharmaceutical effects.

Another object of the invention is to provide an osmotic dosage form comprising encainide that can be admitted into the gastrointestinal tract, wherein the osmotic dosage form substantially reduces and/or substantially eliminates the unwanted influences of the gastrointestinal environment and still provides controlled administration of encainide over time.

Another object of the invention is to provide an osmotic dosage form for oral administration into the gastrointestinal tract where the dosage form releases encainide essentially independent of the GI environment.

Another object of the present invention is to provide a dosage form adapted and designed for oral administration of encainide, which dosage form comprises a first composition and a contacting second composition that cooperate during operation of the dosage form for the rate controlled administration of encainide over time.

Another object of the invention is to provide a dosage form comprising encainide, wherein the dosage form comprises internal means for preventing dose-dumping of encainide from the dosage form.

Another object of the present invention is to provide a complete pharmaceutical regimen comprising a composition comprising a member selected from the group consisting of encainide and its pharmaceutically acceptable salts that can be housed and dispensed from a drug delivery dosage form, the use of which requires intervention only for initiation and possibly for termination of the regimen.

Another object of the invention is to provide a method of treating transient arrhythmias, and to suppress arrhythmias in asymptomatic postinfarction patients by orally administering encainide in a rate controlled dosage per unit time to a warm-blooded animal in need of cardiac therapy.

Other objects, features and advantages of the invention will be more apparent to those versed in the dispensing arts from the following detailed specification, taken in conjunction with the drawings and the accompanying claims.

BRIEF DESCRIPTION OF THE DRAWINGS

In the drawing figures, which are not drawn to scale but are set forth to illustrate various embodiments of the invention, the drawing figures are as follows.

In the drawing figures and in the specification, like parts in related drawing figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
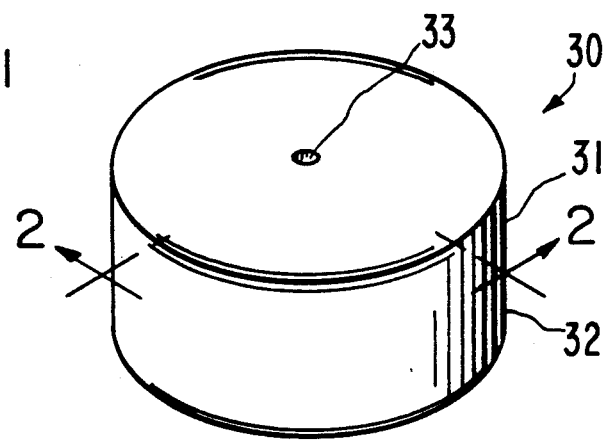
FIG. 1 is a view of a dosage form adapted, designed and shaped for orally administering encainide to the gastrointestinal tract of a warm-blooded animal.

Turning now to the drawing figures in detail, which drawing figure are an example of the dosage form provided by this invention, and which example is not to be construed as limiting, one example of the dosage form is illustrated in FIG. 1 and designated by the numeral 30. In FIG. 1, dosage form 30 comprises a body 31 comprising a wall 32 that surrounds and encloses an internal compartment, not seen in FIG. 1. Dosage form 30 comprises at least one exit means 33 for connecting the interior of dosage form 30 with the exterior environment of use.

Figure 2:
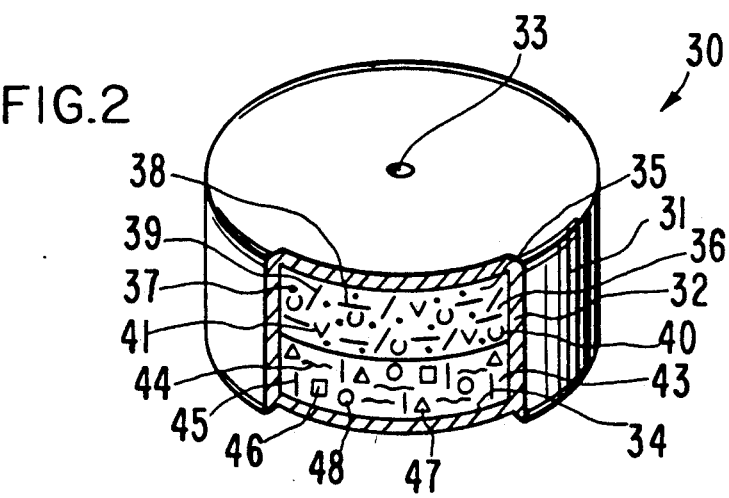
FIG. 2 is an opened view through 2—2 of FIG. 1 for illustrating the internal structure of the dosage form provided by the invention; and, FIGS. 3, 4 and 5 depict the cumulative release pattern for delivery systems prepared by the invention.

In FIG. 2, dosage form 30 is manufactured as an osmotic device, and it is seen in opened view. In FIG. 2, dosage form 30 comprises body 31, a wall 32, that is sectioned at 34, and which wall 32 surrounds and defines an internal compartment 35. Wall 12 comprises at least one exit means 33 that connects compartment 35 with the exterior of dosage form 30. Dosage form 30 can comprise more than one exit means 33.

Wall 32 of dosage form 30 comprises in at least a part a composition that is permeable to the passage of an exterior fluid present in the environment of use. Wall 12 is substantially impermeable to the passage of encainide and other optional ingredients present in compartment 35. Wall 32 comprises a composition that is substantially inert, and it maintains its physical and chemical integrity driving the dispensing life of encainide from dosage form 30. The phrase, "maintains its physical and chemical integrity," means wall 32 does not lose its structure and it does not substantially change during the dispensing life of dosage form 30.

Wall 32 in one presently preferred embodiment comprises in at least a part 100 weight percent (wt%) of a selectively permeable cellulose polymer, or wall 32 in another embodiment comprises in at least a part comprises 65 weight percent to 100 weight percent of a cellulose polymer which polymer comprises a member selected from the group consisting of a cellulose ester, cellulose diester, cellulose triester, cellulose ether, cellulose ester-ether, cellulose acylate, cellulose diacylate, cellulose triacylate, cellulose acetate, cellulose diacetate, cellulose triacetate, cellulose acetate butyrate, and the like. Wall 32 can also comprise from 0 weight percent to 40 weight percent of a cellulose ether member selected from the group consisting of hydroxypropylcellulose and hydroxypropylmethylcellulose, and from 0 weight percent to 20 weight percent of polyethylene glycol. The total amount of all components comprising wall 32 is equal to 100 weight percent. Semipermeable polymers useful for manufacturing wall 32 of dosage form are disclosed in U.S. Pat. Nos. 3,845,770; 3,916,899; 4,008,719; 4,036,228; and 4,111,201. These patents are assigned to the ALZA Corporation of Palo Alto, CA, the assignee of this patent application.

Wall 32, in a more presently preferred manufacture, comprises the selectively permeable cellulose ether, ethyl cellulose. The ethyl cellulose comprises an ethoxy group with a degree of substitution, D.S., of about 1.4 to 3, equivalent to 40% to 50% ethoxy content, and a viscosity range of 7 to 100 centipoise, or higher. More specifically, wall 32 comprises 45 weight percent to 80 weight percent ethyl cellulose, from 5 weight percent to 30 weight percent hydroxypropylcellulose, and from 5 weight percent to 30 weight percent polyethylene glycol, with the total weight percent of all components comprising wall 32 equal to 100 weight percent. In another embodiment 32 comprises 45 weight percent to 80 weight percent of ethylcellulose, from 5 weight percent to 30 weight percent hydroxypropylcellulose, from 2 weight percent to 20 weight percent of polyvinyl pyrrolidone, with the total amount of all components comprising wall 32 equal to 100 weight percent. The ethylcellulose polymer is known in U.S. Pat. No. 4,519,801 assigned to the ALZA Corporation of Palo Alto, CA.

Internal compartment 35, as seen in drawing FIG. 2, comprises a drug composition 36. Drug composition 36 comprises from 5 mg to 300 mg of a member selected from the group consisting of encainide and its pharmaceutically acceptable salts, as represented by dots 37. The drug encainide 37 can be present in the form of its pharmaceutically acceptable salts, such as those formed by hydrochloric acid, hydrobromic acid, sulfonic acid, sulfuric acid, phosphoric acid, acetic acid, propionic acid, citric acid, oxalic acid, maleic acid, gluconic acid, fumaric acid, butyric acid, and the like.

Drug composition 36 comprises also from 10 mg to 200 mg of a polyethylene oxide possessing a 150,000 to 250,000 molecular weight with an average 200,000 molecular weight and identified by dash lines 38, and from 5 mg to 200 mg of a polyethylene oxide possessing a 275,000 to 325,000 molecular weight with an average molecular weight of 300,000 and identified by slant lines 39. The concomitant presence of both polyethylene oxide 38 and polyethylene oxide 39 produces unexpected results for this invention. That is, a drug that is highly water soluble tends to dose-dump in the presence of fluid imbibed into device 30 in the absence of the concomitant presence on polyethylene oxide 38 and polyethylene oxide 39. For example, the drug encainide is highly water soluble, about 303 g/l at 37° C., and it exhibits a tendency to leave dosage form 30 prematurely. The tendency to dose-dump often occurs when dosage form 30 is in operation in a fluid environment of use. The polyethylene oxide 38 and the polyethylene oxide 39 unexpectedly act together to form a viscous solution-suspension in situ comprising the drugs upon inhibition of fluid into dosage form 30. The in situ formation of the viscous solution-suspension comprising the water soluble drug 37 substantially reduces the incidence of dose-dumping, or of a premature mass-release of drug 37. This property of the invention makes possible the controlled delivery of drug 37 at a known rate and in a known amount over time. Drug composition 36 can comprise from 0 mg to 10 mg of a hydroxypropylmethylcellulose, identified by half-circles 40, and having a 9,000 to 22,000 molecular weight, and from 0 mg to 5 mg of a lubricant such as magnesium stearate, stearic acid, and the like, and identified by V-41.

Internal compartment 35, as seen in drawing FIG. 2, comprises a second composition 43. The second composition comprises from 30 mg to 245 mg of a polyethylene oxide comprising a 5,000,000 to 7,800,000 molecular weight and identified by wavy lines 44, from 5 mg to 90 mg of an osmotically effective solute such as sodium chloride and identified by vertical line 45, from 1 mg to 50 mg of a hydroxypropylmethylcellulose having a 9,000 to 22,000 molecular weight and identified by squares 46, from 0.01 mg to 1.5 mg of a lubricant such as magnesium stearate, or stearic acid and identified by triangles 47, and from 0 mg to 40 mg of a carboxyvinyl polymer identified by full circle 48. Second composition optionally comprises from 0 mg to 4.00 mg of colorant ferric oxide.

In the second composition 43, the polyethylene oxide comprising the 7,000,000 to 7,800,000 molecular weight operates in the presence of fluid imbibed into second composition 43 to hydrate, swell and push the first composition 36 from the dosage form 30. The constant pushing against the first composition assures a uniform rate of release of the water soluble drug from the dosage form. Moreover, the presence of the polyethylene oxide 38 and the presence of the polyethylene oxide 39 in the first composition essentially eliminates polyethylene oxide 44 pushing through the first composition and through exit passageway 33 from dosage form 30. The polyethylene oxide comprising a 7,000,000 to 7,800,000 molecular weight is commercially available from the Union Carbide Corporation, South Charleston, WV.

The expression, "exit means 33," as used herein, comprises means and methods suitable for the metered release of beneficial drug 37 from compartment 35 of dosage form 30. The exit means 33 comprises at least one passageway, orifice, or the like, through wall 32 for communicating with drug 37 in compartment 35. The expression, "at least one passageway," comprises aperture, orifice, bore, pore, porous element through which the drug can migrate, hollow fiber, capillary tube, porous overlay, porous insert, and the like. The expression also includes a material that erodes or is leached from wall 32 in the fluid environment of use to produce at least one passageway 33 in dosage form 30. Representative materials suitable for forming at least one passageway, or a multiplicity of passageways, include an erodible poly(glycolic) acid, or poly(lactic) acid member in the wall, a gelatinous filament, poly(vinyl alcohol), leachable materials such as fluid removable pore forming polysaccharides, salts, oxides, or the like. A passageway or a plurality of passageways can be formed by leaching a material such as sorbitol, lactose, fructose and the like from the wall. The passageway can have any shape such as round, triangular, square, elliptical, and the like, for assisting in the metered release of drug 37 from dosage form 30. Dosage form 30 can be constructed with one or more passageways in spaced apart relations, or more than one passageway on a single surface of a dosage form. Passageways and equipment for forming passageways are disclosed in U.S. Pat. Nos. 3,845,770; 3,916,899; 4,063,064 and 4,088,864. Passageways of govern size formed by leaching are disclosed in U.S. Pat. Nos. 4,200,098 and 4,285,987.

The osmotic dosage form of this invention is manufactured by standard techniques. For example, in one embodiment, the beneficial drug is mixed with the polyethylene oxide 38 and the polyethylene oxide 39 and the blend pressed into a solid first composition that possesses dimensions that correspond to the internal dimensions of the compartment space adjacent to a passageway. In another embodiment, the beneficial drug and other nontoxic first composition forming ingredients and a solvent are mixed into a solid, or a semisolid, by conventional methods such as ballmilling, calendering, stirring or rollmilling, and then pressed into a preselected layer-forming shape. Next, the second composition is prepared comprising the polyethylene oxide 44 and the osmagent are placed in contact with the first composition, and the two compositions are surrounded with a semipermeable wall. The layering or lamination of the first beneficial drug composition and the second polyethylene oxide 44 push composition can be accomplished by using a conventional two-layer tablet press technique. The wall can be applied by molding, spraying, or dipping the pressed shapes into the wall forming composition. Another and presently preferred technique that can be used for applying the wall is the air suspension coating procedure. This procedure consists in suspending and in tumbling the two layered laminated laminate in current of air until the wall forming composition surrounds the laminate. The air suspension procedure is described in U.S. Pat. No. 2,799,241; *J. Am. Pharm. Assoc.*, Vol. 48, pp 451-459, (1979) and, ibid. Vol. 49, pp 82-84 (1980). Other standard manufacturing procedures are described in *Modern Plastic Encyclopedia*, Vol. 46, pp 62-70, (1969); and in *Pharmaceutical Sciences*, by Remington, 14th Ed., pp 1626-1978, (1970), published by the Mack Publishing Co., Easton, PA.

Exemplary solvents for manufacturing the wall, the first composition and the second composition include inorganic and organic solvents that do not adversely harm the materials and the final wall or the final compositions in the dosage form. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, usioriotk akcigikm butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

The osmagents, also known as osmotically effective solutes and as osmotically effective compounds that can be used in the first composition or in the second composition comprise organic and inorganic compounds or solutes that exhibit an osmotic pressure gradient across a semipermeable wall. Representative osmagents comprise magnesium sulfate, magnesium chloride, sodium chloride, lithium chloride, potassium sulfate, potassium acid phosphate, mannitol, urea, sucrose, and the like. Osmagents are known to the prior art in U.S. Pat. Nos. 3,854,770; 4,077,407; 4,235,236; and 4,449,983.

DETAILED DESCRIPTION OF EXAMPLES

The following examples are merely illustrative of the present invention and they should not be considered as limiting the scope of the invention in any way as these examples and other equivalents thereof will become apparent to those versed in the art in the light of the present disclosure the drawing and the accompanying claims.

EXAMPLE 1

A dosage form adapted, designed and shaped as an osmotic delivery device is manufactured as follows: first, 233.8 g of the pharmaceutically acceptable polyethylene oxide osmopolymer comprising a 200,000 average molecular weight is passed through a 40 mesh screen, then, 233.8 g of the pharmaceutically acceptable polyethylene oxide osmopolymer comprising a 300,000 average molecular weight is passed through a 40 mesh screen. The two screened osmopolymers next are mixed together and 500 g of drug, such as encainide hydrochloride, and 300 g of pharmaceutically acceptable hydroxypropylmethylcellulose comprising a 10,000 average molecular weight are added thereto. The dry ingredients are mixed for about 10 minutes to produce a homogeneous mass. Then, 870 ml of denatured, anhydrous ethanol is added slowly with further mixing for about 7 minutes. The freshly prepared wet granulation is passed through a 20 mesh screen, dried at room temperature for 16 hours, and again passed through a 20 mesh screen. Finally, the dried granulation is mixed with 2.5 g of magnesium stearate in a rollermill for 5 minutes.

The second composition is prepared as follow: first 200 g of sodium chloride, 10 g of ferric oxide, 50 g of polyacrylic acid polymer, a polymer of acrylic acid crosslinked with 1% of polyallyl ether of sucrose having an average of about 5.8 allyl groups for each molecule of sucrose, as disclosed in U.S. Pat. No. 4,248,857, and 687.5 g of polyethylene oxide comprising a 7,500,000 average molecular weight are passed separately through a 40 mesh screen. Then, the screened ingredients all are mixed with 50 g of hydroxypropylmethylcellulose comprising a 11,200 average molecular weight to produce a homogeneous blend. Then, with constant mixing, 100 ml of denatured anhydrous ethanol is added slowly to the mixing blend. The freshly prepared wet granulation is passed through a 20 mesh screen, allowed to dry at room temperature for 16 hours, and again passed through a 20 mesh screen. The screen granulation is mixed with 2.5 g of magnesium stearate in a rollermill for 5 minutes.

The two compositions that are granulated above are compressed into bilaminate tablets. First 165 mg of the first composition is added to a 0.344 inch punch and tamped, then, 75 mg of the second composition is added and the two laminae are pressed into a contacting laminated arrangement. Then, the bilaminate arrangements are coated with a semipermeable wall. The wall forming composition is compressed of 93% cellulose acetate having an acetyl content of 39.8%, and 7% polyethylene glycol having a 3350 molecular weight. The wall forming composition is dissolved in acetone:water (90:10 wt:wt) solvent to make a 4% solids solution. The wall forming composition is sprayed onto and around the bilaminate in an Aeromatic ® Air Suspension Coater.

Figure 3:
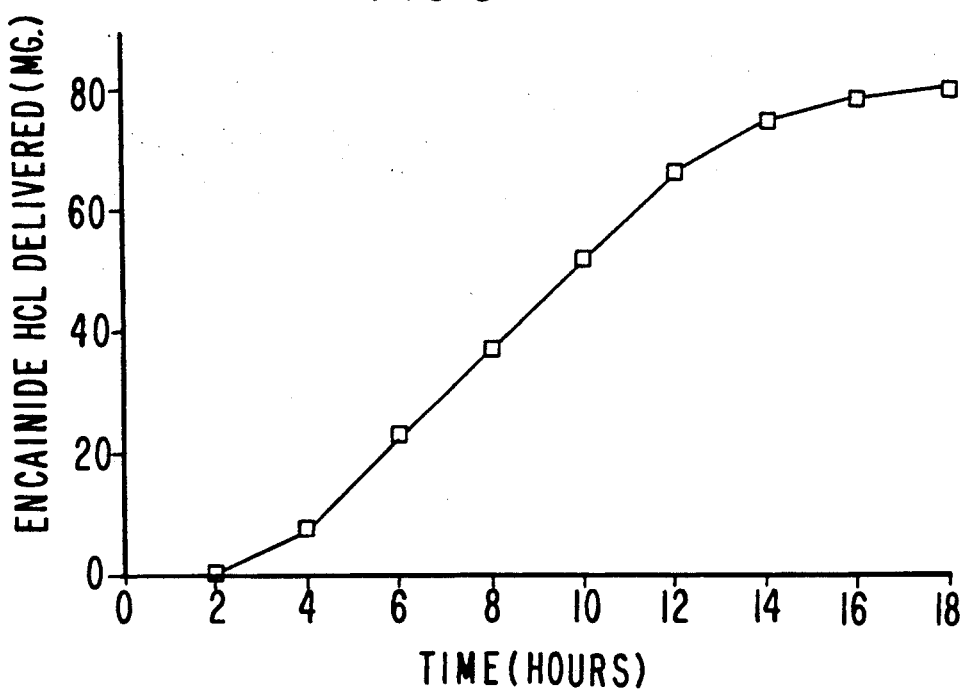

A 25 mil exit orifice is mechanically drilled on the drug side of the osmotic device. The residual solvent is removed by drying the osmotic system for 48 hours at 50° C. and 50% humidity. The osmotic systems are then dried for 1 hour at 50° C. to remove excess moisture. Accompanying FIG. 3 shows the cumulative release profile for the drug encainide of the finished osmotic system as released in distilled water.

EXAMPLE 2

An osmotic dosage form is prepared by following the above procedure with all conditions as set forth. In this example, 230 mg of the first composition is added to a 0.375 inch punch and tamped, and 112 mg of the second composition is added and the two compositions pressed into a contacting laminated arrangement. The delivery system is coated with a wall as described previously. Accompanying FIG. 4 shows the cumulative release profile for the osmotic system as measured in distilled water at 37° C.

EXAMPLE 3

An osmotic dosage form is prepared by following the previous examples, with all conditions as previously described, except that in this example, 330 mg of the first composition is added to a 0.438 inch punch and tamped and 160 mg of the second composition is added to the punch and the two compositions pressed into a bilayer core. The delivery systems are coated with a semipermeable wall and a 25 mil passageway drilled in the wall as described previously. Accompanying FIG. 5 shows the cumulative release profile for the osmotic system measured in distilled water at 37° C. over a 24 hour period of time.

In summary, it will be appreciated that the present invention contributes to the art an unobvious dosage form that possesses practical utility, can administer a drug at a dose metered-release-rate per unit time. While the invention has been described and pointed out in detail with reference to operative-embodiments thereof, it will be understood that those skilled in the art will appreciate that various changes, modifications, substitutions and omissions can be made without departing from the spirit of the invention. It is intended, therefore, that the invention embrace those equivalents within the scope of the claims which follow.

We claim:

1. An improvement in an osmotic dosage form for delivering a drug to an environment of use, wherein the dosage form comprises:
   (a) a wall comprising in at least a part a composition permeable to the passage of fluid, which wall defines and surrounds;
   (b) an internal lumen;
   (c) at least one passageway in the wall that connects the exterior with the interior of the dosage form; and wherein the improvement comprises:
   (d) a first composition in the lumen comprising (1) a dosage amount of a therapeutically acceptable, (2) 10 mg to 200 mg of a polyethylene oxide comprising a 150,000 to 200,000 molecular weight, and (3) 5 mg to 200 mg of polyethylene oxide comprising a 275,000 to 325,000 molecular weight, which polyethylene oxides (2) and (3) act together for substantially lessening the incidence of a premature release of drug from the dosage form; and,
   (e) a second composition in the lumen comprising a polyethylene oxide comprising from 30 mg to 240 mg of a 5,000,000 to 7,800,000 molecular weight, which second composition cooperates with the first composition during operation of the dosage form and displaces the first composition from the dosage form through the passageway in a rate controlled amount over time.

2. An improvement in an osmotic dosage form for delivering the drug according to claim 1, wherein the passageway is formed in the environment of use.

3. An improvement in an osmotic dosage form for delivering the drug, according to claim 1, wherein the passageway is a pore of drug release rate dimensions.

4. An improvement in n osmotic dosage form for delivering the drug according to claim 1, wherein the drug encainide is in the first composition.

5. An improvement in an osmotic dosage form for delivering the drug according to claim 1, wherein the wall is semipermeable and comprises an osmotic pore passageway, and the drug is useful for treating cardiac arrhythmias.

6. An improvement in an osmotic dosage form for delivering the drug according to claim 1, wherein the drug is indicated for the management of patients with ventricular tachycardia, nonsustained ventricular tachycardia, premature ventricular complexes and ventricular arrhythmias.

7. An improvement is an osmotic dosage form for delivering the drug according to claim 1, wherein the drug is a pharmaceutically acceptable salt for treating cardiac arrhythmias.

* * * * *

UNITED STATES PATENT AND TRADEMARK OFFICE
CERTIFICATE OF CORRECTION

PATENT NO. : 5,019,396

DATED : May 28, 1991

INVENTOR(S) : Atul D. Ayer, Anthony L. Kuczynski, Patrick S.L. WONG, Lawrence G. Hamel, Maureen L. Jordan It is certified that error appears in the above-identified patent and that said Letters Patent is hereby corrected as shown below:

In column 8, claim 1, in line 52, after the word "acceptable" insert ----drug----.

In column 9, claim 4, in line 7, after "improvement in" delete "n" and insert therefore ----an----.

Signed and Sealed this

Twenty-ninth Day of September, 1992

*Attest:*

DOUGLAS B. COMER

*Attesting Officer*     *Acting Commissioner of Patents and Trademarks*